United States Patent [19]

Aufdembrink

[11] Patent Number: 4,831,005
[45] Date of Patent: May 16, 1989

[54] METHOD FOR INTERCALATING ORGANIC-SWELLED LAYERED METAL CHALCOGENIDE WITH A POLYMERIC CHALCOGENIDE BY PLURAL TREATMENTS WITH POLYMERIC CHALCOGENIDE PRECURSOR

[75] Inventor: Brent A. Aufdembrink, Voorhees, N.J.

[73] Assignee: Mobil Oil Company, New York, N.Y.

[21] Appl. No.: 140,512

[22] Filed: Jan. 4, 1988

Related U.S. Application Data

[63] Continuation-in-part of Ser. No. 879,787, Jun. 27, 1986, which is a continuation-in-part of Ser. No. 687,414, Dec. 28, 1984, abandoned.

[51] Int. Cl.$^4$ .......................... B01J 21/06; B01J 20/10
[52] U.S. Cl. ..................................................... 502/242
[58] Field of Search ................... 502/242, 350, 77, 63, 502/80; 423/70, 71

[56] References Cited

U.S. PATENT DOCUMENTS 4,600,503  7/1986  Angevine et al. .............. 208/251 H
4,650,779  3/1987  Goldstein .............................. 502/38

Primary Examiner—Carl F. Dees
Attorney, Agent, or Firm—. Alexander J. McKillop; Charles J. Speciale; Edward F. Kenehan, Jr.

[57] ABSTRACT

Organic-swelled layered metal chalcogenides, e.g., titanometallates or silicotitanates, are intercalated with polymeric chalcogenide by plural treatments with hydrolyzable, electrically neutral polymeric chalcogenide precursor, e.g., tetraethylorthosilicate, to provide products of improved surface area.

19 Claims, No Drawings

METHOD FOR INTERCALATING ORGANIC-SWELLED LAYERED METAL CHALCOGENIDE WITH A POLYMERIC CHALCOGENIDE BY PLURAL TREATMENTS WITH POLYMERIC CHALCOGENIDE PRECURSOR

This application is a continuation-in-part of U.S. application Ser. No. 879,787, filed June 27, 1986 which is a continuation-in-part of U.S. application Ser. No. 687,414, filed Dec. 28, 1984 (and now abandoned), the entire contents of both being incorporated herein by reference.

The present invention relates to a method for preparing layered metal chalcogenides containing interspathic polymeric chalcogenides. In one aspect, the invention relates to layered metal oxides which contain interspathic metal oxides, e.g., layered titanium oxides which contain interspathic silica. For the purposes of the invention, the term "metal" can be considered to include the elements boron, silicon, phosphorus and arsenic.

Many layered materials are known which have three-dimensional structures which exhibit their strongest chemical bonding in only two dimensions. In such materials, the stronger chemical bonds are formed in two-dimensional planes and a three-dimensional solid is formed by stacking such planes on top of each other. However, the interactions between the planes are weaker than the chemical bonds holding an individual plane together. The weaker bonds generally arise from interlayer attractions such as Van der Waals forces, electrostatic interactions, and hydrogen bonding. In those situations where the layered structure has electronically neutral sheets interacting with each other solely through Van der Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction mediated by ions located between the layers. In addition, hydrogen bonding interactions can occur directly between complementary sites on adjacent layers, or can be mediated by interlamellar bridging molecules.

Laminated materials such as clays may be modified to increase their surface area. In particular, the distance between the interlamellar layers can be increased substantially by absorption of various swelling agents such as water, ethylene glycol, amines, ketones, etc., which enter the interlamellar space and push the layers apart. However, the interlamellar spaces of such layered materials tend to collapse when the molecules occupying the space are removed by, for example, exposing the clays to high temperatures. Accordingly, such layered materials having enhanced surface area are not suited for use in chemical processes involving even moderately severe conditions.

The extent of interlayer separation can be estimated by using standard techniques such as X-ray diffraction to determine the basal spacing, also known as "repeat distance" or "d-spacing". These values indicate the distance between, for example, the uppermost margin of one layer with the uppermost margin of its adjoining layer. If the layer thickness is known, the interlayer spacing can be determined by subtracting the layer thickness from the basal spacing.

Various approaches have been taken to provide layered materials of enhanced interlayer distance having thermal stability. Most techniques rely upon the introduction of an inorganic "pillaring" agent between the layers of a layered material.

Layered metal chalcogenide materials enjoying thermal stability can be prepared by a method described in U.S. application Ser. No. 879,787, filed June 27, 1986, and incorporated herein by reference. The method comprises: treating a layered chalcogenide, e.g., oxide, of at least one element having an atomic number of 4, 5, 12 to 15, 20 to 33, 38 to 51, 56 to 83 and greater than 90, inclusive, which contains ion exchange sites having interspathic cations associated therewith, with an organic compound which is a cationic species, e.g., n-alkylammonium or capable of forming a cationic species e.g., n-alkylamine, to effect exchange with said interspathic cations in order to swell the layered material. An electrically neutral compound capable of conversion to an interspathic polymeric chalcogenide, e.g., tetraethylorthosilicate, is thereafter provided between the layers of the swelled, layered chalcogenide. The compound is then converted to the interspathic polymeric chalcogenide to form the layered material.

In the past, such layered materials have been prepared by a process wherein residual interlayer water is present in the organic-swelled layered material which is contacted once with electrically neutral organic compound capable of conversion to polymeric chalcogenide to form a pillared product.

However, it has been found that certain organic-swelled layered materials are difficult to intercalate by this procedure, possibly due to poor intercalation of the polymeric chalcogenide precursor, or water needed for hydrolysis, or both. It would be desirable to utilize a technique for preparing layered materials containing interspathic polymeric chalcogenide wherein the incorporation of polymeric chalcogenide precursor is maximized in order to effect enhanced thermal stability and sorption capacity in the final product. It has now been found that layered materials containing an interspathic, i.e., intercalated, polymeric chalcogenide can be prepared even from layered materials which have been difficult to treat by conventional techniques. The method comprises intercalating an organic-swelled layered metal chalcogenide with a polymeric chalcogenide by:

(a) providing between the layers of the layered metal chalcogenide, a polymeric chalcogenide precursor which is an electrically neutral, organic compound capable of conversion to said polymeric chalcogenide by hydrolysis; and converting said compound in the presence of water to the interspathic polymeric chalcogenide and (b) repeating (a) at least once, preferably at least twice, say two or three times.

Water may be added to the layered metal chalcogenide to effect further hydrolysis of the polymeric chalcogenide precursor.

After the plural treatments with the precursor, the resulting material can be calcined to effect further stabilization. The resulting product shows increased surface area and increased sorption capacity for water and $C_6$ hydrocarbons. While not wishing to be bound by theory, it is believed that repeating step (a) serves to remove excess organic swelling agent and hydrolysis by-products from the organic-swelled layered material which allows for incorporation of increased amounts of polymeric chalcogenide precursor between the layers.

For present purposes, polymeric chalcogenides are considered to include chalcogenides of two or more repeating units, preferably three or more repeating units, say four or more or even five or more repeating units. The extent of polymerization of the interspathic polymeric chalcogenide is believed to affect the ultimate interlayer separation of the pillared layered metal oxide product.

The layered chalcogenide material which is organic-swelled to form the organic-swelled starting material employed in the present invention can be a layered oxide, sulfide, selenide or telluride, preferably a layered oxide material of elements other than those of Group VIB of the Periodic Table, i.e., O, S, etc. Suitable layered oxide materials include layered oxides of Group IVA metals such as titanium, zirconium and hafnium, e.g., layered trititanates, such as $Na_2Ti_3O_7$ comprising $Ti_3O_7{}^{-2}$ layers containing intercalated alkali metal as disclosed in U.S. Pat. Nos. 4,600,503, and 2,496,993 incorporated herein by reference. Upon intercalation with polymeric silica, such tritanates are known as silicotitanates. Other layered chalcogenide materials in which the present invention may be used to facilitate intercalation include $KTiTaO_5$ and $Na_4Mn_{14}O_{27}9H_2O$, as well as layered oxides of alumina and silicon such as clays, e.g. bentonite. In particular, the present invention can facilitate intercalation of layered silicates known as high silica alkali silicates whose layers lack octahedral sheets. These silicates can be prepared hydrothermally from an aqueous reaction mixture containing silica and caustic at relatively moderate temperatures and pressures, and may contain tetracoordinate framework atoms other than Si. Included among these materials are magadiite, natrosilite, kenyaite, makatite, nekoite, kanemite, okenite, dehayelite, macdonaldite and rhodesite, preferably their acid-exchanged forms.

Another layered chalcogenide which can be pillared by the present invention is a titanometallate-type layered metal oxide product comprising a layered metal oxide wherein each layer of the metal oxide has the general formula

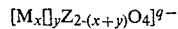

$$[M_x\square_y Z_{2-(x+y)}O_4]^{q-}$$

wherein M is at least one metal of valence n wherein n is an integer between 0 and 7 and preferably is 2 or 3, $\square$ represents a vacancy site, Z is a tetravalent metal, preferably titanium, and wherein $q = 4y - x(n-4)$ and preferably is 0.6–0.9, $0 < x+y < 2$ Interposed between the layers of the starting material oxide will be charge-balancing cations A of charge m wherein m is an integer between 1 and 3, preferably 1. Preferably A is a large alkali metal cation selected from the group consisting of Cs, Rb and K and M is a divalent or trivalent metal cation selected from at least one Mg, Sc, Mn, Fe, Cr, Ni, Cu, Zn, In, Ga and Al. For example, M can be both In and Ga. Structurally, these metal oxides are believed to consist of layers of (M, $\square$, or Z)$O_6$ octahedra which are trans edge-shared in one dimension and cis edge-shaped in the second dimension forming double octahedral layers which are separated by cations in the third dimension. These materials can be prepared by high temperature fusion of a mixture of (1) metal oxide, (2) alkali metal carbonate or nitrate and (3) tetravalent metal dioxide, e.g., titanium dioxide or by fusion of a mixture of alkali metallate and tetravalent metal dioxide. Such fusion can be carried out in air in ceramic crucibles at temperatures ranging between 600° to 1100° C. after the reagents have been ground to an homogeneous mixture. The resulting product is ground to 20 to 250 mesh, prior to the organic swelling and polymeric oxide intercalation steps.

Further description of layered titanometallate starting materials and their methods of preparation can be found in the following references:

Reid, A. F.; Mumme, W. G.; Wadsley, A. D. *Acta Cryst.* (1968), B24, 1228; Groult, D.; Mercy, C.; Raveau, B. *J. Solid State Chem.* 1980, 32 289; England, W. A.; Burkett, J. E.; Goodenough, J. B.; Wiseman, P. J. *J. Solid State Chem.* 1983, 49 300.

Use of these layered metal oxides as the layered starting material permits inclusion of different metal atoms into the layered starting material being treated which allows potential catalytically active sites to be incorporated in the stable layer itself. Moreover, variable amounts of metal atoms may be added to provide a catalyst with optimum activity for a particular process. Furthermore, the infinite trans-edge shared layer structure of the titanometallates-type layered metal oxides instead of the sheared 3-block structure of, for example, $Na_2Ti_3O_7$, may reduce or eliminate shearing of the layers as a possible mechanism for thermal or hydrothermal decomposition of the calcined intercalated material. These titanometallate-type materials may possess even greater thermal stability than silicotitanate molecular sieves. In addition, the variable charge density on the oxide layer possible for these layered metal oxides due to the various oxidation states of metal oxides, the incorporated metal atom and the varying stoichiometry of the materials, may allow variation in the amount of the organic cationic species which can be exchanged into the material. This, in turn, permits variation of the ultimate concentration of the oxide pillars between the layers of the final product.

The metal oxide product contains about 0.5 to about 20 weight percent of said element M, preferably about 1 to 10 weight percent. Vacancy-containing materials (wherein y is greater than zero) are particularly suited for treatment by the present method.

The titanometallate-type layered metal oxide product, after intercalation with polymeric chalcogenide according to the present invention comprises a layered titanometallate-type layered metal oxide and interspathic polymeric chalcogenide of at least one element, separating the layers of the metal oxide. Preferably, such materials after pillaring are thermally stable, i.e., capable of withstanding calcination at a temperature of about 450° C. for at least 2 hours without significant reduction (e.g., not greater than 10 or 20%) in the spacing between the layers.

The organic swelling agent used to swell the layered starting material employed in the present invention comprises a source of organic cation such as organoammonium, which source may include the cation itself, in order to effect an exchange of the interspathic cations resulting in the layers of the starting material being propped apart. In particular, protonated alkylamines are preferred. Often, alkylammonium cations include n-dodecylammonium, n-octylammonium, n-heptylammonium, n-hexylammonium and n-propylammonium.

The source of organic cation in those instances where the interspathic cations include hydrogen or hydronium ions may include a neutral compound such as organic amine which is converted to a cationic analogue during the swelling or "propping" treatment. Among these materials are $C_3$ to $C_{10}$, preferably $C_6$ to $C_8$ alkylamines, preferably n-alkylamines, or $C_3$ to $C_{10}$, preferably $C_6$ to $C_8$ alkanols, preferably n-alkanols. The present method has been found particularly useful in pillaring materials which do not contain interspathic alkali metals, e.g., layered material having ammonium ($NH_4^+$) ions disposed between the layers which are otherwise difficult to pillar.

Interspathic polymeric chalcogenide pillars are then formed between the layers of the organic-swollen layered metal chalcogenide starting material and may include a chalcogenide, preferably a polymeric chalcogenide, of zirconium or titanium or more preferably of an element selected from Group IVB of the Periodic Table (Fischer Scientific Company Cat. No. 5-702-10, 1978), other than carbon, i.e., silicon, germanium, tin and lead. Other suitable chalcogenides include those of the Group VA, e.g., V, Nb, and Ta, those of Group IIA, e.g. Mg or those of Group IIIB, e.g., B. Most preferably, the pillars include polymeric silica. In addition, the chalcogenide pillars may include an element which provides catalytically active acid sites in the pillars, preferably aluminum.

The chalcogenide pillars are formed from a precursor material which is preferably introduced between the layers of the organic "propped" species as a cationic, or more preferably, electrically neutral, hydrolyzable compound of the desired elements, e.g., those of group IVB. The precursor material is preferably an organometallic compound which is a liquid under ambient conditions. In particular, hydrolyzable compounds, e.g., alkoxides, of the desired elements of the pillars are utilized as the precursors. Suitable polymeric silica precursor materials include tetraalkylsilicates, e.g., tetrapropylorthosilicate, tetramethylorthosilicate and, most preferably, tetraethylorthosilicate. Where the pillars are also required to include a different polymeric metal oxide, e.g., alumina or titania, a hydrolyzable compound of said metal can be contacted with the organic "propped" species before, after or simultaneously with the contacting of the propped titanometallate with the silicon compound. Preferably, the hydrolyzable aluminum compound employed is an aluminum alkoxide, e.g., aluminum isopropoxide. If the pillars are to include titania, a hydrolyzable titanium compound such as titanium alkoxide, e.g., titanium isopropoxide, may be used. In addition, the chalcogenide precursor may contain zeolite precursors such that exposure to conversion conditions results in the formation of interspathic zeolite material as at least part of the chalcogenide pillars. Pillars of polymeric silica and polymeric alumina or polymeric silica and polymeric titania are particularly preferred.

After the final hydrolysis to produce the chalcogenide pillars and calcination to remove the organic propping agent, the final pillared product may contain residual exchangeable cations. Such residual cations in the layered material can be ion exchanged by known methods with other cationic species to provide or alter the catalytic activity of the pillared product. Suitable replacement cations include cesium, cerium, cobalt, nickel, copper, zinc, manganese, platinum, lanthanum, aluminum, ammonium, hydronium and mixtures thereof.

The resulting pillared products exhibit thermal stability at temperatures of 500° C. or even higher as well as substantial sorption capacities (as much as 10 to 25 wt% for $H_2O$ and $C_6$ hydrocarbon). Silica-pillared products possess interlayer separations of greater than 12A and surface areas greater that 250 $m^2/g$ when divalent metal atoms, e.g., Mg, Ni, Cu and Zn, are present as the metal M of the product. Silica-pillared products incorporating trivalent metal atoms, e.g., Sc, Mn, Fe, Cr, In, Ga and Al can possess interlayer separations of 6 to 15A.

It has also been found that layered materials containing interspathic polymeric chalcogenide can be improved when their preparation includes conditions which facilitate removal of organic hydrolysis by-products produced during conversion to polymeric chalcogenides. For example, where tetraalkylorthosilicate is used as the organic precursor, alkanols are produced during hydrolysis. By maintaining temperatures which enhance removal of such by-products, the rate and extent of hydrolysis are enhanced. Where tetraethylorthosilicate (TEOS) is used, ethanol is a hydrolysis by-product. By conducting polymeric chalcogenide precursor incorporation and hydrolysis at 50° to 170° C., preferably 75° to 85° C., say about 80° C., pillared products having enhanced crystallinity and interlayer spacings are prepared. Moreover, organic hydrolysis by-products removal can be facilitated by conducting hydrolysis in a system which permits release of the organic hydrolysis by-products from the system. Preferably, such a system contains a means for preventing the introduction of water from outside the system, for example, an outlet tube connected to a silicone fluid bubbler or a Dean and Stark apparatus.

It has also been found that conducting the incorporation of the hydrolyzable organic polymeric chalcogenide precursor between the layers of the layered material and subsequent hydrolysis in an inert atmospheric system reduces extralaminar polymeric chalcogenide formation. Reducing such formation can be advantageous insofar as interior catalytic sites on an intercalated layered material can be obstructed by extralaminar polymeric chalcogenide formation.

The inert atmosphere can be any non-reactive gas, e.g., helium or nitrogen, with nitrogen especially preferred. The non-reactive atmosphere should be substantially free of moisture, say less than about 0.5%, preferably less than 0.01% water in order to prevent extralaminar hydrolysis from occurring. The non-reactive atmosphere may be either static or dynamic. However, where a dynamic system is employed, the flow of inert gas should be low enough to prevent undesired levels of evaporation of the organic polymeric chalcogenide precursor, e.g., tetraethylorthosilicate.

The present invention is illustrated further by the following Examples. In these examples, X-ray diffraction data were obtained by standard techniques using K-alpha doublet of copper radiation. Nitrogen BET surface areas are reported in $m^2/g$.

EXAMPLE 1

Preparation of Layered Titanometallates $CsNO_3$ (53.62 g, 0.2751 mole), $Ni(NO_3)_2 \cdot 6H_2O$ (40.00 g, 0.1375 mole), and $TiO_2$ (51.81 g, 0.6482 mole), were ground to a homogenous mixture. The solids were heated in air to 420° C. for three hours followed by firing at 1000° C. for 12 hours. An X-ray powder pattern of the product agreed with the literature reported for the isostructural compound, $Rb_{0.7}(Mn_{0.7}Ti_{1.3})O_4$ given by Reid, et al. Id. (Interlayer distance=8.41A).

TABLE 1

Preparation of Layered Titanometallate

| Reagent Stoichiometry | Reagents | Rxn Conditions[a] | Product Analysis | d (A)[b] |
|---|---|---|---|---|
| $Cs_{0.70}(Mn_{0.7}Ti_{1.3})O_4$ | $CsMnO_4$, $TiO_2$ | 630° C., 250 min.<br>1000° C., 720 min. | — | 8.57 |
| $Cs_{0.70}(Ni_{0.35}Ti_{1.65})O_4$ | $Cs_2CO_3$, $Ni(NO_3)_2$, $TiO_2$ | 420° C., 200 min.<br>1000° C., 720 min. | $Cs_{0.57}(Ni_{0.32}Ti_{1.70})O_4$ | 8.41 |
| $K_{0.80}(Zn_{0.40}Ti_{1.60})O_4$ | $K_2CO_3$, ZnO, $TiO_2$ | 900° C., 200 min.<br>1050° C., 720 min.<br>regrind, refire | $K_{0.66}(Zn_{0.35}Ti_{1.49})O_4$ | 7.83 |
| $K_{0.80}(Mn_{0.80}Ti_{1.20})O_4$ | $KMnO_4$, $TiO_2$ | 920° C., 600 min.<br>1100° C., 720 min. | $K_{0.69}(Mn_{0.79}Ti_{1.23})O_4$ | 7.76 |
| $K_{0.80}(Fe_{0.80}Ti_{1.20})O_4$ | $K_2CO_3$, $Fe_2O_3$, $TiO_2$ | 900° C., 200 min.<br>1000° C., 720 min. | $K_{0.69}(Fe_{0.73}Ti_{1.28})O_4$ | 7.90 |
| $Cs_{0.70}(Al_{0.70}Ti_{1.30})O_4$ | $Cs_2CO_3$, $Al_2O_3$, $TiO_2$ | 420° C., 180 min. | $Cs_{0.72}(Al_{0.53}Ti_{1.42})O_4$ | 8.84 |
| $Cs_{0.70}([\ ]_{.18}Ti_{1.82})O_4$ | $Cs_2CO_3$, $TiO_2$ | 650° C., 600 min.<br>950° C., 720 min. | — | 8.49 |

[a]All firings were carried out in air.
[b]d-layer spacing from x-ray powder diffraction data.

Additional layered titanometallates were prepared. Reagents, reagent stoichiometries, reaction temperatures, and dwell times are displayed in Table 1 above. The reactions were carried out by thoroughly grinding the reagents to homogenous mixtures and firing in ceramic crucibles. In cases where potassium was used as the alkali metal cation, regrinding and refiring was required to obtain the layered phase in reasonable purity for further reactions. The stiff powders obtained were ground to roughly 100 mesh before further reactions.

EXAMPLE 1a

Ammonium Exchange

The materials of Example 1 containing alkali metal cation were then exchanged with ammonium ion by refluxing three times in 1M $NH_4NO_3$ for 16–24 hr, using from 7–10 ml 1M $NH_4NO_3$/g layered alkali titanometallate. Analytical data is summarized in Table 2.

TABLE 2

| Titanometallate Heteroatom | % N | ppm akali (residual) |
|---|---|---|
| Mn | 3.22 | 525 |
| Zn | 2.24 | 695 |
| Ni | — | — |
| None | — | — |

EXAMPLE 2

Propping Layered Titanometallate by Ion Exchange with Octylammonium Chloride

The interlayer openings in the materials prepared in Example 1 were propped by exchange of the ammonium cations with octylammonium by contacting excess octylammonium (5 equiv octylamine/4.9 equiv HCl/equiv of layered metal oxide) with the layered metal oxide and heating at reflux for 16 to 20 h.

The reaction mixture was cooled, filtered, and washed with hot distilled $H_2O$ (about 2 times the volume of the reaction solution). The solid was air dried at room temperature.

EXAMPLE 2a

Propping Layered Ammonium Titanates By Reaction With Octylamine

Samples from Example 1a were swollen by stirring in neat refluxing octylamine for 16–24 h using at least 5 g octylamine/g solid. The reactions were filtered, washed with 90% EtOH, and air dried. The d-spacings observed for propped materials are summarized in Table 3.

TABLE 3

| Heteroatom | d-spacing (A) |
|---|---|
| Mn | 28.5 |
| Zn | 24.5 |
| Ni | 23.2 |
| None | 25.1, 23.2 |

EXAMPLE 3

Treatment of Swelled Titanometallates with Tetraethylorthosilicate

The octylammonium-swollen solids of Example 2a were stirred in $H_2O$ for 2–4 h, followed by filtration and drying in air. The solids were then stirred in tetraethylorthosilicate (TEOS) at 80° C. for 24 h, filtered and air dried. This sequence was repeated until a very sharp low angle line was observed in the x-ray powder diffraction pattern of the product calcined in air at 500°–510° C. (5° C./min) for 3 h. Results are set out below in Table 4.

TABLE 4

Effect Of Multiple TEOS Treatments On Pillared Titanometallates

| Titanometallate Heteroatom | One TEOS Treatment | | Two TEOS Treatments | | Three TEOS Treatments | |
|---|---|---|---|---|---|---|
| | Interlayer Spacing, d (A) | Surface Area | Interlayer Spacing, d (A) | Surface Area | Interlayer Spacing, d (A) | Surface Area |
| Mn | a | 12 | 18.6 (weak) | 336 | 21.5 (sharp) | 394 |
| Zn | a | 265 | 21.5 | 529 | b | — |
| Ni | 17 | 336 | 21.5 | 516 | b | — |

TABLE 4-continued

Effect Of Multiple TEOS Treatments On Pillared Titanometallates

| Titanometallate Heteroatom | One TEOS Treatment | | Two TEOS Treatments | | Three TEOS Treatments | |
|---|---|---|---|---|---|---|
| | Interlayer Spacing, d (A) | Surface Area | Interlayer Spacing, d (A) | Surface Area | Interlayer Spacing, d (A) | Surface Area |
| None | a | 23 | 20.5 | 431 | b | | a. No low two theta peak observed.
b. Treatment not performed.

The superior properties of the pillared materials thus obtained were dramatic: increased d-spacing of the calcined molecular sieve, increased $SiO_2$ uptake, and larger surface areas resulting in enhanced sorption capacities for $H_2O$ and hydrocarbons.

EXAMPLE 4

Preparation of Layered Silicotitanate

ALL TREATMENTS WERE AT ROOM TEMPERATURE UNLESS OTHERWISE SPECIFIED

A sample of $Na_2Ti_3O_7$ was prepared by calcining an intimate mixture of 1000 g of $TiO_2$ and 553 g $Na_2CO_3$ in air at 1832° F. for 20 hours (5°F./min). The mixture was then reground and reheated in air at 1832° F. for 20 hours (5°F./min). The product was stirred in 1.5 l of water for 1 hour, filtered, dried in air at 250° F. for 1 hour, and calcined in air at 1000° F. for 1 hour. This product was slurried in 900 grams of water and ball-milled for 16 hours. The solid $Na_2Ti_3O_7$ product was filtered and dried for 24 hours.

1,194 grams of this ballmilled product was exchanged 5 times at 185°–195° F. with a solution of 4,240 grams of 50% ammonium nitrate diluted to 10 l with water. The solid product was filtered and washed with 20 l of water after each exchange. The product was dried for 24 hours after the last exchange.

800 grams of the ammonium-exchanged trititanate was refluxed with stirring for 48 hours in a mixture of 800 grams of octylamine in 5,300 grams of water. After that time, another 800 grams of octylamine were added, and the resulting mixture was stirred at reflux for an additional 6 days and then at room temperature for 7 more days. The solution was decanted and the solids filtered using 1 l of ethanol to assist filtration. The product was washed with 20 l of water and dried overnight. 750 grams of this product were refluxed with 1,000 grams of octylamine for 6 hours. The mixture was cooled to 160° F. 1 l ethanol was added, and the product was filtered and dried overnight. This dried material was reslurried in 1 l ethanol for 1 hour, filtered, and dried for 24 hours. The product was then refluxed in 750 grams of octylamine in a 4-necked 5 l round bottom flask equipped with a Dean-Stark trap. Reaction temperature increased in a 1 hour interval from about 275° F. to about 347° F. as water was removed from the system via the Dean-Stark trap. The mixture was refluxed at 347° F. for 2 hours and then cooled to 160° F. Ethanol (one liter) was then added, and the solid product was filtered and dried overnight. The dried product was reslurried in 1 l ethanol for 1 hours, filtered, and dried overnight. This product was then stirred in 3 l water for 24 hours, filtered, and dried for 42 hours. The octylammonium swollen trititanate had the following composition (wt%):

73.1 $TiO_2$
8.97 C
2.3 N
0.116 Na
77.4 Ash 7.5 grams of the octylammonium trititanate was stirred in 50 grams of tetraethylorthosilicate (TEOS) in a 4-necked 125 ml round bottom flask equipped with nitrogen inlet and outlet tubes. The mixture was stirred with a magnetic stirring bar for 3 days under a slow nitrogen purge. The solid product was filtered and dried for 2 hours. A portion of this material was calcined at 950° F. in air for 3 hours. The properties of this material (single TEOS treatment) are given in Table 5.

The uncalcined portion of the product was then stirred in water for 24 h, dried at room temperature for 22 h, retreated with TEOS as described above for 3 days under nitrogen purge and calcined. Properties of the product of single and plural TEOS treatments are set out below in Table 5.

TABLE 5

| | Single TEOS Treatment | TEOS-$H_2O$-TEOS Treatment |
|---|---|---|
| Wt % $SiO_2$ | 11.0 | 19.2 |
| XRD (low 2 theta) | 5.4°, 16.7 A | 3.9°, 22.7 A |
| Surface Area ($m^2/g$) | 145 | 236 |

Repetitive water-TEOS treatments appear to greatly improve pillaring efficiency and product properties in silicotitanate systems.

It is claimed:

1. A method for intercalating an organic-swelled layered metal chalcogenide with a polymeric chalcogenide which comprises:
   (a) providing between the layers of the layered metal chalcogenide an electrically neutral, organic compound capable of conversion to said polymeric chalcogenide by hydrolysis; and converting said compound in the presence of water to the interspathic polymeric chalcogenide and
   (b) repeating (a) at least once.

2. The method of claim 1 wherein (a) is repeated twice.

3. The method of claim 1 wherein the product of (b) is calcined.

4. The method of claim 1 wherein said interspathic polymeric chalcogenide is an interspathic polymeric oxide and said layered metal chalcogenide is a layered oxide.

5. The method of claim 1 wherein said converting is effected by the addition of water.

6. The method of claim 1 wherein said interspathic polymeric oxide comprises polymeric silica.

7. The method of claim 1 wherein said layered metal chalcogenide is titanometallate-type layered metal oxide product comprising a layered metal oxide wherein each layer of the metal oxide has the general formula $$[M_x[]_yZ_{2-(x+y)}O_4]^{q-}$$

wherein M is at least one metal of valence n wherein n is an integer between 0 and 7, [] represents a vacancy site, Z is a tetravalent metal, preferably titanium, and wherein $$q = 4y - x(n-4), \text{ and}$$

$$0 < x+y < 2$$

8. The method of claim 1 wherein said n is 2 or 3 and q ranges between about 0.6 and 0.9.

9. The method of claim 1 wherein said layered metal chalcogenide is a trititanate.

10. The method of claim 9 wherein said titanate comprises $Ti_3O_7^{-2}$ layers.

11. The method of claim 1 wherein said layered metal chalcogenide is a high silica alkali silicate.

12. The method of claim 11 wherein said silicate is selected from the group consisting of magadiite, natrosilite, kenyaite, makatite, nekoite, kanemite, okenite, dehayelite, macdonaldite and rhodesite.

13. The method of claim 12 wherein said silicate is magadiite.

14. The method of claim 1 wherein said electrically neutral compound is tetraalkylorthosilicate.

15. The method of claim 1 wherein said electrically neutral compound is tetraethylorthosilicate.

16. The method of claim 1 wherein said swelling organic is an alkylamine.

17. The method of claim 1 wherein said swelling organic is n-octylamine.

18. The method of claim 1 wherein said swelling organic is an alkylammonium ion.

19. The method of claim 1 wherein said swelling organic is the n-octylammonium ion.

* * * * *